United States Patent
Puskas

(10) Patent No.: US 9,950,168 B2
(45) Date of Patent: Apr. 24, 2018

(54) METHODS FOR INTRACARDIAC SURGERY AND INTRACARDIAC DELIVERY OF THERAPIES AND DEVICES

(71) Applicant: Emory University, Atlanta, GA (US)

(72) Inventor: John D. Puskas, Atlanta, GA (US)

(73) Assignee: EMORY UNIVERSITY, Atlanta, GA (US)

(*) Notice: Subject to any disclaimer, the term of this patent is extended or adjusted under 35 U.S.C. 154(b) by 234 days.

(21) Appl. No.: 14/324,583

(22) Filed: Jul. 7, 2014

(65) Prior Publication Data

US 2015/0012069 A1 Jan. 8, 2015

Related U.S. Application Data

(60) Provisional application No. 61/843,071, filed on Jul. 5, 2013, provisional application No. 61/892,739, filed on Oct. 18, 2013.

(51) Int. Cl.
*A61N 1/36* (2006.01)

(52) U.S. Cl.
CPC ...... *A61N 1/36114* (2013.01); *A61N 1/36053* (2013.01)

(58) Field of Classification Search
CPC ............ A61N 1/36114; A61N 1/36053; A61B 2017/00243; A61B 17/00
USPC .... 607/62, 116; 604/96, 272, 507, 508, 523, 604/532; 606/194
See application file for complete search history.

(56) References Cited

U.S. PATENT DOCUMENTS

| | | | | |
|---|---|---|---|---|
| 4,314,550 A | * | 2/1982 | Apstein | A61B 17/00 128/DIG. 3 |
| 5,766,151 A | * | 6/1998 | Valley | A61B 17/00234 604/103.07 |
| 6,711,436 B1 | * | 3/2004 | Duhaylongsod | A61K 31/00 600/16 |
| 2007/0093748 A1 | * | 4/2007 | Nayak | A61B 17/3478 604/93.01 |

* cited by examiner

*Primary Examiner* — Christopher D Koharski
*Assistant Examiner* — Roland Dinga
(74) *Attorney, Agent, or Firm* — Parks IP Law LLC

(57) ABSTRACT

A method of performing an intracardiac procedure using controlled intermittent diastolic arrest (CIDA) to expand the chambers of the heart to a volume between about 75 to 200% of their normal end-diastolic volume. In one embodiment, CIDA is conducted so that cardiac arrest with cardiac distention is achieved in about 5 to 15 seconds and diastolic arrest is maintained for a time between about 5 and 90 seconds. Intracardiac procedures that are facilitated with CIDA include heart valve repair or replacement. The method involves the use of CIDA and wherein the procedure is performed in or on the heart with the use of a catheter or catheter-delivered device, therapy, or agent. In one aspect, the heart is accessed during CIDA via a left ventricular apical access port or device. In one aspect CIDA is conducted via stimulation of the vagal nerve alone or in combination with one or more of an acetylcholinesterase inhibitor, a β-adrenergic receptor blocker, and/or a calcium channel blocker.

20 Claims, No Drawings

METHODS FOR INTRACARDIAC SURGERY AND INTRACARDIAC DELIVERY OF THERAPIES AND DEVICES

BACKGROUND OF THE INVENTION

The field of the invention is intracardiac procedures. More specifically the present disclosure provides methods for improved intracardiac surgery and intracardiac delivery of therapies and devices.

Intracardiac procedures are most easily performed on a heart that is not beating or that has minimal blood flow therethrough. Cardiopulmonary bypass and chemical arrest using cardioplegia solutions have traditionally provided surgeons with suitable operative conditions: hemodynamic control and cardiac quiescence. This technique has contributed to technical success in increasingly complex cardiac surgical operations. However, it would be advantageous to have methods for conducting intracardiac procedures with the heart in a blood-filled but non-beating state.

Surgeons have also used cardioplegia, fibrillators, or clamps to stop blood flow in their working field. Adenosine has been shown to be safe and effective in creating transient cardiac standstill and has been used during balloon coronary and valvular dilatation procedures and implantation of stents and grafts. Another method of producing a heart without blood flowing therethrough is rapid ventricular pacing.

Rapid ventricular pacing causes the heart to beat at approximately 200 to 400 beats/min, which functionally means that the heart is in continuous contraction, never fills with blood between beats, and therefore the flow of blood through the heart is stopped. Rapid ventricular pacing produces a heart that is in contractile, rigid "arrest" and has the disadvantage of not providing a generous intracardiac space in which to work. Rapid ventricular pacing is functionally "systolic arrest". It stresses the myocardium to contract so rigorously and repeatedly and this may induce myocardial injury, especially when prolonged rapid pacing is performed in patients with hypertrophic or ischemic myocardium.

Another method that creates brief periods of heart stillness is taught in U.S. Pat. No. 6,479,523 and related patents. This patent teaches methods for creating controlled intermittent asystole (CIA) and using CIA during brief intervals required for placing anastomotic sutures. This method is taught to be especially useful for use in placing anastomotic sutures during minimally invasive direct coronary artery bypass (MIDCAB) surgery, for example. CIA is suitable for improving the precision of coronary anastomoses performed on a beating heart and reducing graft failure while increasing ease of operation. This patent does not discuss in detail the use of CIA for minimally invasive intracardiac access or procedures.

It has now been discovered that controlled intermittent asystole can be employed by minimally invasive means to specifically enable novel catheter-based intracardiac technologies and therapies by placing the heart in a relaxed state, in which its chambers are intentionally distended by passive inflow of blood and thereby expanded to create generous working space within the cardiac chambers. This creates an intracardiac environment in which the surgeon has better access to intracardiac anatomic structures and adequate space in which to maneuver instruments, catheters, and imaging devices. The motionless, relaxed, capacious state of the heart during CIA is in sharp contrast to the variable state of the heart during normal beating or its hypercontracted state during rapid ventricular pacing.

This particular method of "controlled intermittent asystole" is termed "controlled intermittent diastolic arrest" (CIDA) herein. The heart is placed in an intentional state of inactivity with the chambers expanded and filled with blood for the purposes of performing intracardiac procedures such as valvular repair or replacement, ventricular remodeling procedures, implantation of intracardiac devices, therapeutics, gene therapy, stem cell therapy, angiogenic therapy etc., rather than epicardiac procedures, such as coronary artery bypass grafting.

SUMMARY OF THE INVENTION

The present invention involves a method of performing an intracardiac procedure using controlled intermittent diastolic arrest (CIDA). CIDA is conducted to cause expansion of the chambers of the heart to a volume between about 75 to 200% of their normal end-diastolic volume. In one embodiment, CIDA is conducted so that cardiac arrest with cardiac distention is achieved in about 5 to 15 seconds and diastolic arrest is maintained for a time between about 5 and 90 seconds.

Intracardiac procedures that are facilitated with CIDA include heart valve repair or replacement, mitral valve repair or replacement, aortic valve repair or replacement, pulmonic valve repair or replacement, and tricuspid valve repair or replacement.

The method involves the use of CIDA and wherein the procedure is performed in or on the heart with the use of a catheter or catheter-delivered device, therapy, or agent. In one aspect, the heart is accessed during CIDA via a left ventricular apical access port or device. In one aspect CIDA is conducted via stimulation of the vagal nerve alone or in combination with one or more of an acetylcholinesterase inhibitor, a β-adrenergic receptor blocker, and/or a calcium channel blocker.

DETAILED DESCRIPTION OF THE INVENTION

CIDA (controlled intermittent diastolic arrest) is especially useful for enabling novel techniques and therapies which can be better performed when there is space within the cardiac chambers to maneuver. Presently, for intracardiac procedures, the heart is left beating, slowed slightly with pharmaceutical drugs such as beta blockers, or rapidly paced to stop flow. Rapid ventricular pacing actually reduces space within the left and right ventricles, because the heart is squeezing virtually all the time—the interval between beats is so small that the heart never relaxes and fills (and hence why rapid pacing stops blood flow). CIDA does the opposite and stops the heart in a relaxed, dilated state.

CIDA (controlled intermittent diastolic arrest) is employed to create "diastolic arrest" for the purpose of conducting an intracardiac procedure. CIDA is triggered using vagal nerve stimulation (VNS) alone or in combination with drug therapy. CIDA facilitates intracardiac access and procedures because it causes the heart to stop beating and simply relax. The heart naturally fills with blood (i.e., the pump is primed, which is the purpose of diastole) and dilates/distends. Since the heart is not beating during CIDA, there is no flow of blood through the heart and therefore intracardiac delivery of devices and therapies is facilitated.

Intracardiac procedures which can be performed using CIDA include, but are not limited to, delivering and/or positioning an intracardiac device to repair, modify, or replace a heart valve (including the aortic, mitral, pulmonic, and tricuspid valves), techniques to restore or improve the geometry of a chamber of the heart, techniques to repair a cardiac defect (such as an atrial septal defect, ventricular septal defect, other congenital cardiac anomalies, etc.), and techniques to close an apical access hole. CIDA can also be employed to allow delivery of an agent into the heart, into a coronary artery, or into a portion of the tissue of the heart, including medications, stem cells, gene therapy, growth factors, other factors to facilitate regeneration of part(s) of the heart, and acellular matrices for tissue engineering of the heart. CIDA can be performed to facilitate cardioscopy. CIDA can also be used to facilitate diagnostic and therapeutic electrophysiology procedures for the treatment of atrial and/or ventricular arrhythmias, including atrial fibrillation, atrial flutter, ventricular tachycardia, ventricular fibrillation, aberrant conduction pathways and various re-entrant arrhythmias. CIDA may be useful to facilitate the positioning of pacemaker and defibrillator leads into specifically desired locations of the heart, including the coronary sinus or targeted sites on the left or right ventricular endocardium.

It should be understood that while this disclosure is directed to the use of CIDA for intracardiac procedures, it can also be used to facilitate epicardial procedures (or combined intracardiac and epicardiac procedures). For example, placement of sutures or a device to close an apical access hole can be performed either intracardially or epicardially. The use of CIDA to cause the heart to stop beating and simply relax facilitates both means of placing sutures or devices.

CIDA may be accomplished by vagal nerve stimulation alone or stimulation of autonomic nerve fibers near or within the heart itself, and such stimulation may be accompanied by administration of one or more drugs to potentiate the physiological impact of the vagal or autonomic nerve stimulation, U.S. Pat. No. 6,479,523 teaches achieving CIA using unilateral (or bilateral) vagal nerve stimulation optionally coupled with pharmacologic suppression of electromechanical escape activity and the methods taught therein can in general be used in the present invention.

Vagal nerve stimulation can be achieved by direct or indirect electrical stimulation. CIDA can be produced by vagal nerve stimulation alone if short periods of time (1-5 seconds) are needed. If longer time periods of diastolic arrest are desired (5-90 seconds), vagal nerve stimulation can be combined with treatment with an acetylcholinesterase inhibitor (A), and/or a β-adrenergic receptor blocker (B), and/or a calcium channel blocker (C), or various combinations thereof.

The stimulation of the vagal nerve can be in a variety of locations such as by using skin electrodes or electrode collars, direct cut-down onto the nerve in the neck or in the chest, trans-jugular (trans-venous), trans-carotid, trans-tracheal, trans-esophageal, or any bipolar combination of these possible sites.

The access point for catheter-based delivery of medications, treatments, or devices may be via an artery, a vein, or directly into a part of the aorta, great vessels, or a part of the heart. Intracardiac delivery of therapies and devices may be via a catheter-based technique or via a direct surgical approach. It may be percutaneous catheter delivery, minimally invasive surgical delivery, or via an open surgical approach.

Specific Applications of CIDA:
Catheter Delivery of Devices and Therapies to Repair or Replace the Mitral Valve Mitral valve repair and replacement are procedures performed to treat stenosis (narrowing) or regurgitation (leakage) of the mitral valve. The mitral valve is the valve between the left atrium and left ventricle. Blood flows from the lungs, where it picks up oxygen, through the pulmonary veins, to the left atrium of the heart. After the left atrium fills with blood and subsequently contracts, the mitral valve allows blood to flow from the left atrium into the left ventricle. It then closes to keep blood from leaking back into the left atrium or lungs when the left ventricle contracts (squeezes) to push blood through the aortic valve, out of the heart to the body. The mitral valve generally has two flaps, or leaflets. Repair of the mitral valve can include placement of a ring around the valve to bring the leaflets into contact with each other (annuloplasty), removal of redundant/loose segments of the leaflets (quadrangular or other leaflet resection), re-suspension of the leaflets with artificial chords, chord repair, and placement of a mitral clip or other device to hold the leaflets together or close clefts in leaflets through which leakage occurs. In addition, the entire valve can be replaced with a mitral valvular prosthesis.

Recent noninvasive catheter-based techniques access the mitral valve through the femoral vein and a trans-septal puncture from the right atrium to the left atrium. In a preferred embodiment of the method, CIDA is used to intermittently induce diastolic arrest and expansion of the heart chambers, specifically the left atrium and ventricle, before, during, or after threading of the catheter from the right atrium into the left atrium. Alternatively, the mitral valve may be approached via the left ventricular apex. An access port may be inserted into the left ventricular apex and instruments and catheters may be introduced through the port into the left ventricle, gaining direct access to the mitral valve. In another preferred embodiment, the creation of the left ventriculotomy and insertion of a left ventricular apical port are facilitated by the use of CIDA to induce diastolic arrest, relaxing the left ventricular apical free wall and expanding the size of the left ventricular chamber. Via the left ventricular apex, instruments may be inserted directly into the left ventricle and repair/replacement of the mitral or aortic valve or ascending aorta may be accomplished, all enabled by CIDA.

One or more brief periods (10-30 seconds) of CIDA allows the catheter operator to identify the optimal site for trans-septal puncture and then to puncture the catheter through the interatrial septum, passing from the right atrium to the left atrium. Once a suitable catheter has been advanced into the left atrium, it can be used to inspect the mitral valvular apparatus and to perform the desired repair such as correcting central mitral regurgitation by "capturing" the anterior and posterior leaflets with a clip-like device or correcting chordal rupture by repairing chords or replacing them with artificial chords. CIDA may be used to provide a controlled period(s) of dilated cardiac quiescence to facilitate "capture" of the papillary muscle(s) for anchoring/attachment of an artificial chord(s). This may require single or multiple episodes of CIDA lasting 5-60 seconds.

Similarly, "capture" of the mitral annulus for attachment/insertion of a mitral annuloplasty device is facilitated by multiple episodes of CIDA, each lasting 5-60 seconds. A mitral annuloplasty device may require multiple points of attachment to the mitral annulus; each point of attachment may be secured to the mitral annulus with catheter-delivered fixation devices (screws, rivets, sutures, wires, springs, snaps etc) and each may be most easily delivered during a brief period of CIDA, lasting 5-60 seconds.

Choosing the optimal size for a mitral valve annuloplasty device can be difficult, at least in part because the mitral annulus is a dynamic structure during normal cardiac contractions. Thus, CIDA will facilitate sizing of the mitral annulus to optimize correct sizing of the prosthetic annuloplasty device. This may require a brief 10-30 second period of CIDA, allowing the heart to fill and then measuring the dimensions of the mitral annulus (and mitral leaflet(s)) with the heart in a full and quiescent state. Finally, the diastolic distention created during CIDA can be used to assess the quality of mitral valve repair or replacement. Assessed by a catheter in the left atrium (or by intraoperative echocardiogram) the amount of leaking of blood through the mitral valve will be very small (or zero) if the repair is optimal; significant residual leaking will indicate a need for further repair or replacement.

Transcatheter Aortic Valve Replacement

In another preferred embodiment of the method, CIDA is used to facilitate transcatheter aortic valve replacement (TAVR). Noninvasive repair of the aortic valve can be accomplished via femoral artery access, transapically (through the wall of the heart), via axillary/subclavian artery access (beneath the collar bone), and direct aortic access (through a minimally invasive surgical incision into the aorta).

In a preferred embodiment of the method, CIDA is initiated to induce diastolic arrest and expansion of the heart chambers, specifically the left atrium and left ventricle, before, during, or after threading of the catheter through the aortic valve and into the left ventricle (in the case of transfemoral, subclavian, axillary, carotid and aortic access). CIDA is also useful for passing the catheter into the apex of the heart and from the left ventricle through the aortic valve and into the aorta (in the case of transapical access). Regardless of the route of catheter access to the aortic valve, CIDA will facilitate the positioning and expansion of the balloon catheter used for balloon aortic valve dilation that precedes transcatheter aortic valve replacement. Moreover, CIDA will eliminate the contraction of the left ventricular outflow tract muscle that may hinder balloon aortic valve dilation, and thereby improve the dilation, facilitating optimal sizing of the aortic valve prosthesis and reducing the extent and incidence of paravalvular regurgitation. Similarly, the cessation of blood flow provided by CIDA will facilitate correct positioning and ease of deployment of the transcatheter aortic valve prosthesis itself within the aortic valve annulus. This is vitally important to minimize risk of malpositioning of the device, which can result in coronary artery obstruction, causing myocardial infarction or embolization of the valve prosthesis with catastrophic consequences. In addition the very careful sizing of the aortic valve annulus necessary to choose the optimal size prosthesis, is facilitated by a brief period of CIDA (5-15 sec), during which fluoroscopy can document optimal annular size.

Aortic valves have sometimes been delivered via cannulation of the right carotid artery via a small incision in the neck (for patients whose femoral vessels are too small or calcified to pass the devices up from the groin). Such a small incision in the neck would also provide direct access to the vagus nerve (indeed, the surgeon has to literally move the vagus nerve out of the way to get to the carotid artery during such an operation). In this case, the electrodes disclosed in U.S. Pat. No. 7,840,278 that were designed for direct application to the vagal nerve may be the device of choice.

Similarly, a surgeon sometimes makes a small incision (2 inches) through the top part of the sternum (manubrium only) to deploy an aortic valve via direct puncture into the aorta. The vagus nerve lies just to the right of the aorta, deep to the posterior pericardium at that level and can be accessed directly for vagal nerve stimulation to accomplish CIDA to enable such a procedure without using rapid ventricular pacing. Alternatively, the VN may be stimulated in this region via electrodes mounted on specially designed endotracheal tubes, such as those disclosed in U.S. Pat. No. 7,072,720 and U.S. Pat. No. 7,840,278. Patients in whom access to the aorta is achieved by an incision in the manubrium will be intubated and under general anesthesia; such an endotracheal electrode array may be a preferred means of stimulating the VN in such patients.

Of course, virtually all patients undergoing an intracardiac procedure will have a jugular venous central line (IV catheter) inserted into the right and/or left internal jugular vein. Specially designed intravenous catheters with expandable electrode arrays disclosed in U.S. Pat. Nos. 7,072,720 and 7,840,278, will be the preferred minimally invasive means of stimulating the VN in many patients to accomplish CIDA.

Cardioscopy

Cardioscopy is a new technique of inserting a long catheter-like device into the heart (through multiple possible access routes) that has a camera and a special lens and optical system that can see through blood. It has the potential to enable vision-guided procedures inside the heart. To date the technique has been used in a beating heart but the present method expands the use of the technique to a non-beating, relaxed heart.

CIDA is used to stop the heart beating in a diastolic state, so that the chambers are expanded and visibility is not impeded by movement. CIDA facilitates cardioscopy in multiple ways: by creating adequate working space to insert the visualization device and having it "stand off" from the cardiac structure of interest so as to increase field of view. During cardioscopy, visualization of intracardiac structures is facilitated if a "nose cone" can displace blood from between the camera tip and the intracardiac object of interest. CIDA increases the room in which such a "nose cone" may be deployed and utilized. In addition, CIDA facilitates cardioscopy by producing a motionless, filled heart, so that cardiac structures are not beating against the cardioscope; this avoids trauma to cardiac structures that is a concern during cardioscopy performed on a hearting heart. Finally, CIDA allows cardioscopy in the "full" diastolic phase of the cardiac cycle, permitting careful assessment of the geometric relationship of intracardiac structures when the heart is full. This will be vitally important to judging the optimal length and position of artificial mitral chords, among other therapies. Of course, CIDA also includes the ability to return to a normal beating-heart state, which allows assessment of the intracardiac structures and devices during systole as well.

Cardioscopy may be used before, during, and/or after a procedure such as valve repair or the other procedures described herein and the present invention includes the use of CIDA at different times in a procedure, using conditions effective for the stage. For example, CIDA could be initiated to enhance visualization of a mitral valve prior to valve repair. CIDA could then be employed, perhaps under different conditions, during the valve repair to allow more effective valve repair.

Closure of an Apical Access Hole

Some cardiac procedures are performed through an access hole in the left or right ventricular apex. After such transapical catheter-based cardiac surgical and cardioscopic procedures the hole is closed with sutures or by the placement of a closure device. These sutures and devices are difficult to place using rapid ventricular pacing, because the heart is tense and quivering.

CIDA can be employed to facilitate the placement of sutures or other closure devices to close the apical access hole. CIDA will provide a relaxed, quiescent state of the heart during which sutures can be more safely and accurately placed to close the apical puncture site. CIDA may be used to place each suture and again to tie each suture, since tension on the suture will be less likely to result in the suture tearing through the heart tissue if the tissue is relaxed at the time the suture is placed and at the time the suture is tied. CIDA may be useful during placement of sutures both epicardially and intracardially.

Devices used to close an apical access hole currently include corkscrew-like plugs, bi-lobe inflatable balloon devices, and others, and more devices are being developed. Most of these devices are delivered intracardially via catheters, but may be placed by an epicardiac approach. CIDA can be employed to position or deploy or tighten each of these devices.

Other Applications for CIDA

CIDA can be employed for many other intracardiac procedures when a nonbeating heart is advantageous. In addition to mitral valve and aortic valve repair and replacement, as discussed above, it can be used to facilitate tricuspid or pulmonary valve procedures. CIDA can be used to allow intracardiac tissue excision such as excision of hypertrophic muscle or septal myectomy. CIDA can be used to facilitate intracardiac procedures such as gene therapies, stem cell therapies, tissue regeneration therapies, and intracardiac injection of other bio-active agents. CIDA could also be used to enable repair of ventricular aneurysms and pseudoaneurysms and facilitate electrophysiology procedures for ablation of atrial or ventricular fibrillations and other aberrant pathways.

Combination of Procedures

As discussed above for cardioscopy, CIDA can be used during different portions of a procedure, such as during visualization during cardioscopy and then during the procedure itself.

Creation of CIDA

Because CIDA is essentially a prolonged diastole, it causes the heart chambers to expand to a size that is larger than the normal end-diastolic size of the heart chambers, up to 200% of the normal end-diastolic size of the heart. Thus, CIDA provides a larger working area inside the heart than can be achieved with other methods of achieving cardiac standstill. Different intracardiac procedures may benefit from differing degrees of cardiac distention, which can be provided in a controlled way by inducing CIDA for various periods of time. The surgeon or interventional cardiologist may use imaging modalities such as transthoracic echocardiography, transesophageal echocardiography, x-ray (cine-) fluoroscopy or direct cardioscopy (with direct or fiberoptic imaging technologies or echo-enhanced technologies) to assess the optimal distention of the heart which will optimally facilitate the intended intracardiac procedure. This may require a series of several trial episodes of CIDA to identify the optimal duration of CIDA. For instance, the mitral leaflets are in subtly different positions in relation to the left ventricular free wall, the aortic valve and each other at differing degrees of ventricular distention. Optimal localization and subsequent mechanical "capture" of mitral leaflets may be most easily achieved when the attempt at capture is made within relatively specific time intervals from onset of CIDA, corresponding to relatively specific degrees of left ventricular diastolic distention. This will be determined by trial and error for each patient, but will likely fall into ranges of duration of CIDA that facilitate specific intracardiac procedures for most/all patients.

In preferred embodiments of the invention, intracardiac procedures are conducted after CIDA is employed to induce heart stillness in diastole. While CIDA provides immediate cessation of the heart beat when vagus nerve stimulation is initiated, the filling of the heart to reach full end-diastolic dimensions is achieved in about 5 to 15 seconds and can then be maintained by CIDA for a time between about 15 and 90 seconds, at the discretion of the operator. The size of the heart—especially the left ventricle—during CIDA arrest is from about 75 to 200% of its normal end-diastolic volume, preferably about 100 to 150% of its normal end-diastolic volume. Periods of mechanical heart standstill can be timed to coincide with periods of intracardiac maneuvering. Periods of standstill up to about 90 seconds can be achieved, most reliably up to about 60 seconds. After each period of standstill, the heart beat is restored for a few beats in order to provide the patient with adequate blood circulation. This pattern can be repeated indefinitely.

In general, the procedures and devices disclosed in U.S. Pat. Nos. 6,479,523 and 7,840,278 can be used in the presently disclosed methods for intracardiac surgeries and delivery. Controlled CIDA is created by vagal nerve stimulation, preferably coupled with pharmacological suppression of electromechanical escape activity. Pharmacological agents include an acetylcholinesterase inhibitor (A), a β-adrenergic receptor blocker (B), and/or a calcium channel blocker (C). CIDA can be created through vagal nerve stimulation (VNS) alone, with A or B or C or AB or AC or BC or ABC.

To achieve consistent asystole, nerve stimulation of the right vagus nerve before or after treatment with the pharmacological combinations of the present invention has been preferred, although stimulation of the left vagus nerve, or of the distal cardiac branches of the right (or left) vagus nerve are alternative methodologies, incorporated herein. Electrical stimulation is carried out on the right or left vagus nerve, preferably at a site in the neck, thoracic inlet or mediastinum. Other suitable locations for vagal nerve stimulation include, but are not limited to, unipolar or bipolar electrical stimulation of the right or left vagus nerve, or both, stimulation of the vagus nerve in the chest after sternotomy, stimulation with a percutaneous catheter or electrode probe in the internal jugular vein, carotid artery, esophagus, trachea, or a cutaneous electrode array or by a combination of these. The nerve stimulator is typically a Grass wire with a single point of contact, but other suitable stimulators include a pair of pacing wires or electrodes placed about 1 cm apart to allow bipolar prodromic stimulation. A single continuous impulse is applied of between about 5 seconds to about 90 seconds, preferably between about 5 seconds and about 30 seconds. Impulse parameters can readily be varied, e.g., a frequency range of between about 1 Hz and about 500 Hz, preferably between about 20 Hz to about 80 Hz, more preferably about 40 Hz, with an amplitude between about 1 to about 40 volts. Arrays of electrodes may be deployed on specially designed catheters within the internal jugular vein, carotid artery, esophagus, trachea, carotid sheath, or on the skin to stimulate the vagus nerve(s) for the purposes of inducing and maintaining CIDA.

Conditions are selected to provide the desired time period of heart stillness and also the desired end-diastolic volume for the specific intracardiac procedure/technique being performed, as mentioned above.

Pharmacologic Potentiation

Acetylcholinesterase inhibitors (A) are also known as cholinesterase inhibitors. Suitable acetylcholinesterase inhibitors include, but are not limited to tacrine hydrochloride, pyridostigmine bromide, neostigmine methylsulfate, and edrophonium chloride. One preferred acetylcholinesterase inhibitor is pyridostigmine bromide. Acetylcholinesterase inhibitors are administered in a dosage range between about 0.01 mg/kg and about 100 mg/kg, preferably between about 0.1 mg/kg and about 2.0 mg/kg, more preferably about 0.5 mg/kg.

Beta-adrenergic receptor blockers are also known as beta-adrenergic blocking agents. Suitable beta-adrenergic receptor blockers include, but are not limited to, sotalol HCl, timolol maleate, esmolol hydrochloride, carteolol hydrochloride, propranolol hydrochloride, betaxolol hydrochloride, penbutolol sulfate, metoprolol tartrate, acetbutolol hydrochloride, the combination of atenolol and chlorthalidone, metoprolol succinate, pindolol, and bisoprolol fumarate. One preferred beta-adrenergic receptor blocker is propranolol hydrochloride. Beta-adrenergic receptor blockers are administered in a dosage range between about 0.01 mg/kg and about 100 mg/kg, preferably between about 0.01 mg/kg and about 2.0 mg/kg, more preferably about 80 µg/kg.

Suitable calcium channel blockers include, but are not limited to, nifedipine, nicardipine hydrochloride, diltiazem HCl, isradipine, verapamil hydrochloride, nimodinpine, amlodipine besylate, felodipine, bepridil hydrochloride, and nisoldipine. One preferred calcium channel blocker is verapamil hydrochloride. Calcium channel blockers are administered in a dosage range of between about 0.001 mg/kg to about 1 mg/kg, preferably between about 0.01 mg/kg and about 0.2 mg/kg, more preferably about 0.05 mg/kg.

It will be understood that other dosage combinations may be effective. The appropriate dosage is determined by the age, weight, sex, health status of the patient, cardiac disease, and preexisting cardiac conduction abnormalities, and may vary with a variety of other factors according to conventional clinical practice.

Several suitable devices for achieving CIDA are disclosed in U.S. Pat. No. 7,840,278. The devices direct an electrical pulse of optimized intensity and duration at a selected position along the nerve, and thereby induce cardiac quiescence. Spontaneous escape from asystole is prevented pharmacologically. The heart beat can be restored immediately after cessation of vagus nerve stimulation by using the "slaved" cardiac pacer system disclosed in U.S. Pat. No. 7,840,278 incorporated in its entirety herein.

Modifications and variations of the present invention will be apparent to those skilled in the art from the forgoing detailed description. All modifications and variations are intended to be encompassed by the following claims. All publications, patents, and patent applications cited herein are hereby incorporated by reference in their entirety.

What is claimed is:

1. A method, comprising:
    conducting controlled intermittent diastolic arrest (CIDA) comprising:
        stimulating, by a stimulator, a vagal nerve for a first amount of time; and
        applying, by an application device, at least one pharmacological agent, wherein the first amount of time and the at least one pharmacological agent are selected to achieve a diastolic distension volume of at least a portion of a heart for a second amount of time; and
    restoring, by a restoring system, a heart beat of the heart after:
        a third amount of time during which the at least a portion of the heart fills and expands to reach the diastolic distension volume; and
        the second amount of time at which the least the portion of the heart is at the diastolic distension volume.

2. The method of claim 1, wherein the diastolic distension volume is 75 to 200% of a normal end-diastolic volume.

3. The method of claim 2, wherein the diastolic distension volume is 100 to 150% of the normal end-diastolic volume.

4. The method of claim 2, wherein the third amount of time is 5 to 15 seconds.

5. The method of claim 1, wherein the second amount of time is 5 to 90 seconds.

6. The method of claim 5, wherein the second amount of time is about 60 seconds.

7. The method of claim 1, further comprising performing, by a intracardiac procedure device while heart is at the diastolic distension volume for the second amount of time, an intracardiac procedure, wherein the intracardiac procedure includes a heart valve repair or replacement of at least one of a mitral valve, an aortic valve, a pulmonic valve, a tricuspid valve.

8. The method of claim 1, further comprising performing, by a intracardiac procedure device while heart is at the diastolic distension volume for the second amount of time, an intracardiac procedure, wherein the intracardiac procedure includes at least one of:
    cardioscopy;
    creation or closure of an apical access hole with sutures; and
    insertion of an apical access port or device.

9. The method of claim 1, further comprising performing, by an intracardiac procedure device while the heart is at the diastolic distension volume for the second amount of time, an intracardiac procedure, wherein the intracardiac procedure is one that is performed at least one of:
    in or on the heart is performed with the use of at least one of a catheter or catheter-delivered device, therapy, or agent; and
    via a left ventricular apical access port or device, with an instrument, catheter, or device or therapy introduced into the left ventricle via a left ventricular apex of the heart.

10. The method of claim 1, further comprising performing, by an intracardiac procedure device while heart is at the diastolic distension volume for the second amount of time, an intracardiac procedure, wherein the intracardiac procedure is at least one of:
    a diagnostic or therapeutic electrophysiology procedure to diagnose or treat a cardiac arrhythmia; and
    the delivery of an active agent to the heart.

11. The method of claim 10, wherein the active agent is a medication, stem cell, gene therapy, growth factor, angiogenic factor, other factor to facilitate regeneration of part of the heart, or acellular matrix for tissue engineering of the heart.

12. The method of claim 1, wherein the pharmacological agent is at least one of an acetylcholinesterase inhibitor, a beta-adrenergic receptor blocker, and a calcium channel blocker.

13. A method, comprising:
conducting at least one trial controlled intermittent diastolic arrest (CIDA), comprising:
conducting, by a CIDA system comprising at least a stimulator device and a restoring system, the at least one trial CIDA for an amount of time; and
determining, by an imaging device, a degree of cardiac chamber distension during the at least one trial CIDA arrest;
associating, by the CIDA system, an optimal degree of cardiac chamber distention for performing an intracardiac procedure with the amount of time where the determined degree of cardiac chamber distention is the optimal degree of cardiac distension; and
performing, by the CIDA system, CIDA for an amount of time based on a selection of at least one of an optimal degree of cardiac chamber distention and the intracardiac procedure.

14. A system for conducting controlled intermittent diastolic arrest (CIDA), comprising:
a stimulator configured to stimulate a vagal nerve for a first amount of time; and
an application device configured to apply at least one pharmacological agent, wherein the first amount of time and the at least one pharmacological agent are selected based on achieving a diastolic distension volume of at least a portion of a heart for a second amount of time; and
a restoring system configured to restore a heartbeat of the heart after:
a third amount of time during which the at least a portion of the heart fills and expands to reach the diastolic distension volume; and
the second amount of time at which the least the portion of the heart is at the diastolic distension volume.

15. The system of claim 14, wherein the diastolic distension volume is 75 to 200% of a normal end-diastolic volume.

16. The system of claim 14, wherein the third amount of time is 5 to 15 seconds.

17. The system of claim 14, wherein the second amount of time is 5 to 90 seconds.

18. The system of claim 14, further comprising an intracardiac procedure device configured to perform, while heart is at the diastolic distension volume for the second amount of time, an intracardiac procedure, wherein the intracardiac procedure includes at least one of:
a heart valve repair or replacement of at least one of a mitral valve, an aortic valve, a pulmonic valve, a tricuspid valve;
cardioscopy;
creation or closure of an apical access hole with sutures; and
insertion of an apical access port or device;
a diagnostic or therapeutic electrophysiology procedure to diagnose or treat a cardiac arrhythmia; and
the delivery of an active agent to the heart; or wherein the intracardiac procedure is one that is performed at least one of:
in or on the heart is performed with the use of at least one of a catheter or catheter-delivered device, therapy, or agent; and
via a left ventricular apical access port or device, with an instrument, catheter, or device or therapy introduced into the left ventricle via a left ventricular apex of the heart.

19. The system of claim 18, wherein the active agent is a medication, stem cell, gene therapy, growth factor, angiogenic factor, other factor to facilitate regeneration of part of the heart, or acellular matrix for tissue engineering of the heart.

20. The system of claim 14, wherein-the pharmacological agent is at least one of an acetylcholinesterase inhibitor, a beta-adrenergic receptor blocker, and a calcium channel blocker.

* * * * *